United States Patent
Tryggestad et al.

(10) Patent No.: US 9,254,112 B2
(45) Date of Patent: Feb. 9, 2016

(54) RESPIRATORY INTERVAL-BASED CORRELATION AND PROCESSING OF DYNAMIC IMAGING DATA

(75) Inventors: Erik John Tryggestad, Baltimore, MD (US); Steven Michael Shea, Baltimore, MD (US); Teboh Roland, Baltimore, MD (US)

(73) Assignee: SIEMENS CORPORATION, Iselin, NJ (US)

( * ) Notice: Subject to any disclaimer, the term of this patent is extended or adjusted under 35 U.S.C. 154(b) by 795 days.

(21) Appl. No.: 13/344,667

(22) Filed: Jan. 6, 2012

(65) Prior Publication Data

US 2012/0245453 A1 Sep. 27, 2012

Related U.S. Application Data

(60) Provisional application No. 61/466,688, filed on Mar. 23, 2011.

(51) Int. Cl.
| | | |
|---|---|---|
| A61B 5/05 | (2006.01) | |
| A61B 6/00 | (2006.01) | |
| A61B 5/055 | (2006.01) | |
| G01R 33/567 | (2006.01) | |
| A61B 5/00 | (2006.01) | |
| G01R 33/483 | (2006.01) | |
| G01R 33/563 | (2006.01) | |

(52) U.S. Cl.
CPC ............... *A61B 6/5288* (2013.01); *A61B 5/004* (2013.01); *A61B 5/055* (2013.01); *A61B 6/463* (2013.01); *A61B 6/486* (2013.01); *A61B 6/541* (2013.01); *G01R 33/5673* (2013.01); *G01R 33/5676* (2013.01); *A61B 6/544* (2013.01); *G01R 33/4835* (2013.01); *G01R 33/56308* (2013.01)

(58) Field of Classification Search
None
See application file for complete search history.

(56) References Cited

U.S. PATENT DOCUMENTS

| | | | |
|---|---|---|---|
| 2003/0088174 A1* | 5/2003 | Sussman et al. | 600/410 |
| 2010/0130849 A1* | 5/2010 | Tao et al. | 600/410 |
| 2011/0148928 A1* | 6/2011 | Gopalakrishnan et al. | 345/643 |
| 2012/0027272 A1* | 2/2012 | Akinyemi et al. | 382/128 |

OTHER PUBLICATIONS

Abdelnour et al., "Phase and Amplitude binning for 4D-CT Imaging", Physics in Medicine and Biology, 2007, pp. 3515-3529.*
Chavarrias et al., "Validation of a retrospective respiratory gating method for small animal CT scanners", 2008 IEEE Nuclear Science Symposium Conference Record, pp. 4303-4305.*
Adamson et al., Maximum intensity projection (MIP) imaging using slice-stacking MRI. Medical Physics, vol. 37, No. 11. pp. 5914-5920 (Nov. 2010).
Blackall et al., MRI-based measurements of respiratory motion variability and assessment of imaging strategies for radiotherapy planning, Phys Med Biol. 51. pp. 4147-4169 (2006).

(Continued)

*Primary Examiner* — Christopher Cook

(57) ABSTRACT

A method of dynamic imaging and resolving respiratory motion includes acquiring volume data for a volume over a plurality of respiratory cycles, acquiring respiratory data representative of respiration over the plurality of respiratory cycles, dividing each respiratory cycle of the plurality of respiratory cycles into a set of respiratory intervals based on the respiratory data, and displaying a respective composite three-dimensional image of the volume for each respiratory interval based on the volume data acquired during the respiratory interval from each respiratory cycle of the plurality of respiratory cycles.

19 Claims, 11 Drawing Sheets

(56) References Cited

OTHER PUBLICATIONS

Cai et al., Evaluation of the reproducibility of lung motion probability distribution function (PDF) using dynamic MRI, Phys Med Biol. 52, pp. 365-373 (2007).

Cai et al., Estimation of error in maximal intensity projection-based internal target volume of lung tumors: a simulation and comparison study using dynamic magnetic resonance imaging, Int J Radiat Oncol Biol Phys. 69, pp. 895-902 (2007).

Cai et al., Reproducibility of interfraction lung motion probability distribution function using dynamic MRI: statistical analysis, Int J Radiat Oncol Biol Phys. 72, pp. 1228-1235 (2008).

Cai et al., The effect of respiratory motion variability and tumor size on the accuracy of average intensity projection from four-dimensional computed tomography: an investigation based on dynamic MRI, Med Phys. 35, pp. 4974-4981 (2008).

Cai et al., Effects of breathing variation on gating window internal target volume in respiratory gated radiation therapy, Med Phys. 37, pp. 3927-3934 (2010).

Dinkel et al., 4D-MRI analysis of lung tumor motion in patients with hemidiaphragmatic paralysis, Radiother Oncol. 91, pp. 449-454 (2009).

Ford et al., Respiration-correlated spiral CT: A method of measuring respiratory-induced anatomic motion for radiation treatment planning, Med. Phys. 30, pp. 88-97 (2003).

Lu et al., A semi-automatic method for peak and valley detection in free-breathing respiratory waveforms, Med Phys. 33, pp. 3634-3636 (2006).

Olson et al., Effect of novel amplitude/phase binning algorithm on commercial four-dimensional computed tomography quality, Int. J. Radiation Oncology Biol. Phys., vol. 70, No. 1, pp. 243-252 (2008).

Persson et al., Deviations in delineated GTV caused by artefacts in 4DCT, Radiother. Oncol. 96, pp. 61-66 (2010).

Remmert et al., Four-dimensional magnetic resonance imaging for the determination of tumour movement and its evaluation using a dynamic porcine lung phantom. Phys. Med. Biol. 52, pp. N401-N415 (2007).

Sarker et al.. Variations in tumor size and position due to irregular breathing in 4D-CT: a simulation study. Med. Phys. 37, pp. 1254-1260 (2010).

Tokuda et al., Adaptive 4D MR Imaging Using Navigator-Based Respiratory Signal for MRI-Guided Therapy, Mag. Resonance in Med., 59, pp. 1051-1061 (2008).

Z von Siebenthal et al.. 4D MR imaging of respiratory organ motion and its variability, Phys. Med. Biol. 52, pp. 1547-1564 (2007).

Watkins et al., Patient-specific motion artifacts in 4DCT, Med Phys. 37. pp. 2855-2861 (2010).

\* cited by examiner

RESPIRATORY INTERVAL-BASED CORRELATION AND PROCESSING OF DYNAMIC IMAGING DATA

CROSS-REFERENCE TO RELATED APPLICATION

This application claims the benefit of U.S. provisional application entitled "Method for 2D-to-4D retrospective sorting of dynamic MRI images," filed Mar. 23, 2011, and assigned Ser. No. 61/466,688, the entire disclosure of which is hereby incorporated by reference.

BACKGROUND

The present embodiments relate to dynamic medical imaging systems.

Magnetic resonance imaging (MRI) and computed tomography (CT) are medical imaging techniques in widespread use for viewing the structure and function of the human body. MRI systems provide soft-tissue contrast, which may be useful for diagnosing soft-tissue disorders, such as tumors. CT is an image processing technique that generates a three-dimensional (3D) image from a large number of two-dimensional (2D) X-ray projections.

Radiation therapy, or radiotherapy, has relied on MRI and CT to direct radiation at malignant tumors as part of cancer treatments. The information provided by the images helps determine a 3D dose distribution and avoid damage to surrounding tissue. Unfortunately, radiotherapy is hampered by motion and deformation of the organs in the thoracic and abdominal cavities, e.g., the lungs, liver and pancreas, during respiration. Such organ motion may lead to a discrepancy between planned and actual target positions. Until recently, there were no readily available imaging modalities capable of resolving and rendering respiratory motion in four dimensions, the fourth dimension being time. A typical strategy to account for respiratory motion used conventional CT, along with a generic uncertainty margin, to define a target volume for radiotherapy treatments delivered with patients breathing freely. A limitation of this technique is that the uncertainty margins are typically conservative (overly large and non-patient-specific), which leads to sub-optimal target conformality and thus more radiation dose to normal tissues.

More recently, radiotherapy treatments have become increasingly sophisticated with better imaging and targeting methods. In so called "respiratory gating" techniques, respiration is monitored during imaging and treatment. One such technique acquires or retrospectively samples images at a particular portion of the respiratory cycle, e.g., typically near end of normal exhalation. The same "gating window" is then used for the treatment delivery. By acquiring CT images or slices throughout a full respiratory cycle at each nominal slice location, time-resolved, or four-dimensional (4D), X-ray computed tomography ("respiratory-correlated CT" or "4D-CT") images are derived. 4D-CT images have been used to define patient-specific target volumes in connection with lung and abdominal radiotherapy and for dose planning.

4D-CT typically samples a single respiratory cycle at each slice location. As a result, slice-to-slice and phase-to-phase consistency of the 4D-CT image reconstruction relies on anatomic reproducibility in the breathing cycle. Irregular breathing leads to volume inconsistencies and geometric reconstruction artifacts. Furthermore, temporal limitations in CT image acquisition (mainly due to restrictions of gantry speed) oftentimes result in intra-phase residual motion, which tends to increase apparent volumes of tumors and contextual anatomy around the inhale (higher-velocity) portion of the respiratory cycle. Attempts to address these limitations with repeated 4D-CT acquisition may expose the patient to increased levels of ionizing radiation.

Dynamic MRI has been used to resolve respiratory motion. MRI procedures are not limited by concerns regarding radiation exposure. Dynamic MRI sequences can provide higher effective frame rates than 4D-CT, minimizing residual intra-phase motion. However, dynamic 3D MRI acquisitions are not yet suitable given present limitations in either signal-to-noise ratio (SNR), spatial resolution, or frame rate.

2D dynamic MRI images have also been used to resolve respiratory motion. For example, 2D slices have been stacked to generate a time-resolved, 3D liver volume. The volumes are retrospectively sorted by searching for similar anatomic liver states. See von Siebenthal et al., "4D MR imaging of respiratory organ motion and its variability," Phys. Med. Biol., Vol. 52, pp. 1547-1564 (2007). This technique may suffer from lack of extendibility to other sites of disease, and from a lower effective frame rate.

SUMMARY

By way of introduction, the embodiments described below include methods, systems, and apparatuses for resolving respiratory motion of a tumor or other tissue volume. Images over a plurality of respiratory cycles are correlated and processed in accordance with respiratory phase or amplitude, which may be referred to as respiratory bins or respiratory intervals.

In a first aspect, a method of dynamic imaging and resolving respiratory motion includes acquiring volume data for a volume over a plurality of respiratory cycles, acquiring respiratory data representative of respiration over the plurality of respiratory cycles, dividing each respiratory cycle of the plurality of respiratory cycles into a set of respiratory intervals based on the respiratory data, and displaying a respective composite 3D image of the volume for each respiratory interval based on the volume data acquired during the respiratory interval from each respiratory cycle of the plurality of respiratory cycles.

In a second aspect, a system for dynamic imaging and resolving respiratory motion, the system includes a respiratory monitor to acquire surrogate respiratory data over a plurality of respiratory cycles, a scanner to acquire frame data over the plurality of respiratory cycles, the frame data including a plurality of frames, and one or more processors in communication with the respiratory monitor and the scanner, the one or more processors being configured to divide each respiratory cycle of the plurality of respiratory cycles into a set of respiratory intervals based on the surrogate respiratory data and being further configured to construct a respective composite 3D image for each respiratory interval based on the frames acquired during the respiratory interval from each respiratory cycle of the plurality of respiratory cycles.

In a third aspect, a magnetic resonance imaging (MRI) apparatus includes an MRI scanner configured to acquire data representing a plurality of 2D slices over a plurality of respiratory cycles, and a control system in communication with the MRI scanner and configured to direct the MRI scanner to implement a series of pulse sequences configured to scan the plurality of 2D slices, the control system including one or more processors configured to divide each respiratory cycle of the plurality of respiratory cycles into a set of respiratory intervals and being further configured to construct a respective composite 3D image for each respiratory interval based on the data representing the 2D slices acquired during the respiratory interval from each respiratory cycle of the plurality of respiratory cycles.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PRESENTLY PREFERRED EMBODIMENTS

Figure 1:
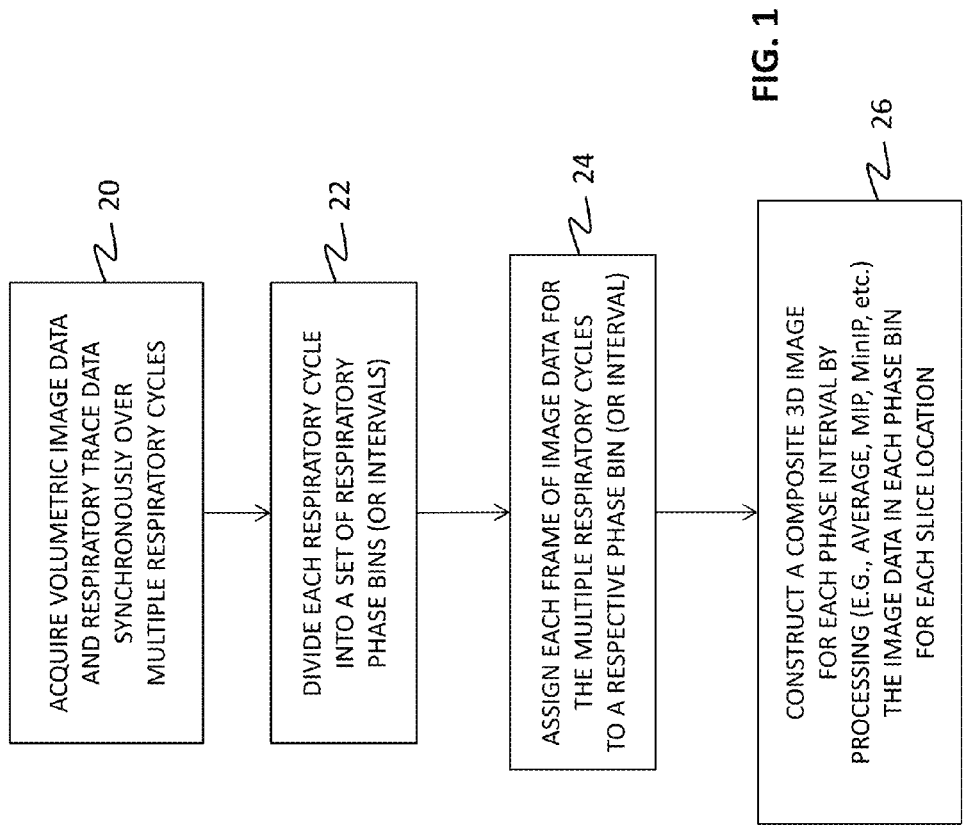
FIG. 1 is a flow diagram of an example embodiment of a method of dynamic imaging for resolving respiratory motion of a 3D volume from image and respiratory data over multiple respiratory cycles.

Imaging methods, systems, computer-readable storage media, and apparatus are provided for correlating and processing scanned, framed, or volume data based on respiratory interval. The volume data produced by the methods and systems may form a set of 3D images depicting anatomy (e.g., tumors and surrounding normal tissue) at various portions of respiration. The images may be used for radiotherapy treatment planning and delivery optimization. Volume data over multiple respiratory cycles may be retrospectively sorted in accordance with respiratory interval. In some cases, the volume data includes 2D dynamically acquired data, such as dynamic MRI slices. The retrospective stacking and processing of MRI slices generates, or reconstructs, a 4D representation that addresses variability between respiratory cycles. The reconstructed 4D image set is derived in a robust way, with minimal user interaction, for use during radiation treatment or radiation treatment planning. Acquisition and processing of image and respiratory data over a multitude of respiratory cycles may allow for a better 4D representation of average breathing motion and capture variations in respiratory motion.

The imaging methods and systems may combine two different sorting procedures for resolving respiratory motion. One or both of respiratory surrogate-based sorting via a respiratory signal and internal-anatomy based sorting may be used. The respiratory surrogate data may provide a temporal or probability gauge with which to generate a representation of an average breathing cycle, while the anatomy-based sorting may refine image quality.

The imaging methods and systems may use 2D MRI sequences (e.g., balanced steady-state free precession, half-Fourier-acquisition single-shot turbo spin-echo (HASTE), etc.), which achiever more clinically useful frame rates, signal-to-noise ratios (SNR), and spatial resolution. The imaging methods and systems may be used for anatomic and/or "real time" applications, and may be used for imaging the thorax, abdomen, or other anatomy. The images of respiratory motion on a per-patient basis may be used to localize a target each day of treatment. More robust or correct 4D images may allow for more sophisticated motion-compensation techniques to be employed and radiotherapy treatment volumes may shrink as a result. The shrinkage may facilitate dose escalation to improve local tumor control, as well as reduce effects on normal tissue, in thoracic, abdominal, or other sites.

The methods and systems may include one or more respiration-correlated averaging procedures to address the variability, or non-reproducibility, present in respiration. The images generated by the methods and systems may be free from, or subject to less, slice-to-slice geometric inconsistencies that would otherwise be present for irregular breathers. Averaging the slice or volume data based on respiratory interval may further improve signal-to-noise ratio (SNR) and therefore enhance clinical utility. Other composite representations of the slice or volume data may be produced via image processing as an alternative or addition to averaging.

In some embodiments, retrospective 2D-to-4D sorting of sagittal or coronal frames acquired using dynamic MRI sequences is performed. Respiratory-correlated MRI or "4D-MRI" volumes are determined using a two-pass approach. In the first pass, a respiratory signal is acquired simultaneously with slice or volume data. The slice or volume data may be processed and slice stacked to render a set of 3D images, each image representing an equal-time or equal-probability portion (or interval) of a respiratory cycle. All frames associated with a given respiratory interval are averaged, which produces composite images with good signal-to-noise ratio (SNR) characteristics. The second-pass sorting technique may improve contrast, or reduce blurring, in the composite images produced by the first pass. The second pass may use a normalized cross-correlation or other image registration comparison, with the results from the first-pass reconstruction providing a set of template images. The subset of the raw 2D frames that best match the template images are selected for averaging, per slice location and phase bin. Such sorting and processing may reduce image blurring without significant sacrifices in SNR. The resulting 3D images for the set of respiratory intervals may be more reliable for image segmentation in radiotherapy planning.

Although described below in connection with 2D raw MRI images, the disclosed methods, systems, and devices are not limited to any particular imaging modality. The image correlation and processing techniques may be applied to any dynamically acquired images, including 3D MRI images (e.g., single-shot techniques). The images may thus be acquired and presented in slices, frames, or other formats used by the imaging modality. The retrospective slice stacking techniques are well suited for use with images not necessarily arranged as slices. X-ray computed tomography (CT) is one example of an alternative modality suitable for use with the methods described herein.

FIG. 1 depicts a dynamic imaging method for resolving respiratory motion via respiratory signal-based image correlation and processing. Slice or volume data is correlated and processed to sort the data temporally in accordance with respiratory data. The dynamic imaging method may retrospectively sort and process slice or volume data based on respiratory data (e.g., respiratory trace) to construct (or reconstruct from raw slice or volume data) a number of 3D composite images of a volume of interest over time, i.e., a 4D representation of the volume that resolves the respiratory motion. In this example, raw 2D slice data is acquired in act 20 for a plurality of slice locations or planes that collectively form a 3D image data set for a volume of tissue. This acquisition over the plurality of slices may then be repeated over time. The 2D data may be acquired via an MRI scanner implementing one or more conventional MRI sequences, including, but not limited to, for example, true fast imaging with steady state precession (TrueFISP), HASTE, turbo fast low angle shot (FLASH), or single-shot echo-planar imaging (EPI). Each slice has a respective plane, the orientation of which may vary depending on the imaging sequence. For example, the slices may be oriented along a sagittal, coronal, or both axes, for the volume. The data need not be acquired and/or arranged in slices or 2D frames. For instance, the data may be arranged in 3D frames. In one example, the data may be acquired via a single-shot MRI or other sequence that produces 3D data.

The volume data includes multiple frames. In 2D MRI embodiments, the volume data includes multiple frames for each slice location. In a 3D modality, such as 3D MRI, the volume data includes multiple 3D frames of the tissue volume. In 2D embodiments, the sorting includes stacking the slices to form the 3D images.

The volume data is acquired over multiple respiratory cycles. The number of respiratory cycles may be large, insofar as the image acquisition sequence may be repeated. The repetition of the image acquisition sequence may also be large, such as in embodiments that do not use ionizing radiation. For example, the image acquisition may be implemented continuously for approximately 10-30 minutes, providing data over hundreds of respiratory cycles. As a result, the image acquisition includes multiple 2D slices for each respiratory stage, segment, interval, or other portion of the respiratory cycle. As described below, such portions of the respiratory cycle may be defined by the phase of the respiratory cycle. The respiratory cycles may be defined between successive inspiratory peaks. Other phases or points in the respiratory cycle may also be used as a trigger point for defining the beginning and ending points of each respiratory cycle. The data acquisition may, but need not be, gated or otherwise timed to coincide with a respiratory cycle or phase.

Data indicative of respiration, or respiratory trace, is also acquired in act 20 during data acquisition. Respiratory data may be acquired synchronously with the image acquisition. The respiratory data provides a surrogate for the respiration, which, in turn, allows the slice or volume data to be sorted temporally or in a probabilistic fashion to form a 4D image set. Such respiratory-based sorting also organizes the data in preparation for image processing in accordance with the methods described herein.

Respiratory data may be acquired via one or more techniques. In some embodiments, the respiratory data is acquired by capturing and sampling an external respiratory surrogate signal. A variety of devices or procedures may be used to generate the respiratory surrogate signal. In one example, a pneumatic belt worn by the patient is used to produce the respiratory surrogate signal. A signal generated by the belt may be transmitted to a controller or other equipment (see, e.g., FIG. 5) that processes the incoming image data. Such processing may include time stamping or other correlation of the respiratory data and the slice or volume data. The respiratory and slice or volume data may be time-stamped via a common clock. Alternative respiratory data acquisition techniques include image-based techniques, in which, for example, one-dimensional or 2D navigator (or tracking) images are acquired during the slice or volume data acquisition. The navigator images may focus on, for example, an anatomical feature in the abdomen that moves with respiration, such as the diaphragm. Other acquisition techniques include infrared (IR)-based respiratory phase monitors, such as the REAL-TIME POSITION MANAGEMENT™ (RPM) system commercially available from Varian Medical Systems, Inc., or the LED-based device onboard the CYBERKNIFE radiotherapy system used for SYNCHRONY modes of treatment delivery (Accuray, Inc.). Any one or more of these techniques may provide the surrogate data indicative of patient respiration.

The respiratory data is processed in act 22 to define the respiratory cycles as well as a set of respiratory phase intervals, or phase bins, for each respiratory cycle. In this example, each respiratory cycle is divided into a set of respiratory phase intervals based on an analysis of the respiratory data. The respiratory signal may be sampled, filtered or otherwise processed to remove noise in preparation for the analysis. The sampling may include down-sampling or up-sampling, as in the examples described below. The analysis may include processing to determine the frequency of the respiratory signal (e.g., an average frequency over the imaging session) based on the sampled representation. The analysis may alternatively or additionally include the generation of a moving average representation of the respiratory signal. Such analysis of the respiratory data may be implemented via a procedure having instructions written in, for instance, a programming language, such as C++, Java, C#, MATLAB (The MathWorks, Inc., Natick. Mass.), or via other software or computer-based procedures. One or more portions or segments of the respiratory data may be removed from the analysis in the interest of avoiding noisy or otherwise unreliable signals. For example, the data collected during or at the end-exhale minima of the respiratory cycle may be corrupted by interference from cardiac noise and, thus, not incorporated into the analysis. In some embodiments, signal processing techniques may be alternatively or additionally used to eliminate or mitigate cardiac interference in the respiratory signal.

The analysis of the respiratory data may be used to determine a trigger or point at which the respiratory cycles may be defined as beginning. In one example, the trigger for each cycle is the peak inspiratory maximum. Other points in the respiratory cycle may alternatively be used as a trigger or cycle-defining event. Once the peak inspiratory maxima (or other trigger points) define each of the respiratory cycles in the data acquisition session, each respiratory cycle is segmented, discretized or otherwise divided into the set of respiratory intervals, or bins. Each interval may be of equal time length for a given respiratory cycle, or may be defined on the basis of equal-likelihood over the duration of imaging. Thus, the number of intervals available in each respiratory cycle does not vary, but the width placement and ordering of the intervals may vary from cycle to cycle. The number of respiratory intervals may be selected as a parameter of the image processing method, and may be, for example, between 8 and 15. The number may vary or be dependent, in part, on the raw imaged frame rate, or, for example, on the available 2D or 3D images from which to generate a final 4D representation.

The data frames, or images, may then be assigned to, or correlated with, respective respiratory intervals in act 24. Each respiratory interval may be considered a bin into which image data is assigned based on the time at which the image data was captured. Given the time stamp or other indication of the timing of the slice or volume frame, each slice or volume captured during the imaging session falls within one of the discretized segments established by the respiratory intervals (e.g., bins 1-12) of one of the respiratory cycles. With every respiratory cycle divided into the same number of intervals, each acquired slice or volume frame is correlated with or assigned to one of them. The number of frames of imaging data in each respiratory bin may vary. As a result, the number of frames available for image processing may also vary between slices and bins.

One or more composite images are then derived or constructed in act 26 for each respiratory interval or bin. The image derivation may include one or more image processing procedures on the raw slice or volume data correlated with each respiratory phase interval. The image processing may include one or more procedures or techniques that involve selection, combination, or comparison of the raw slice or volume data in each phase bin. For example, the raw slice or volume data for each respiratory interval may be averaged to form the composite image(s) for each respiratory interval. In embodiments with 2D data, the averaging for each respiratory interval is implemented on a slice-by-slice or frame-by-frame basis. A set of 2D composite images may thus be derived for each respiratory interval, each slice having a respective composite image. The 2D composite images may then be stacked to form a 3D composite image for each respiratory phase. In other embodiments, such as 3D MRI, the image data may be averaged over a different or entire portion of the imaged volume. In 3D embodiments, a single 3D composite image is derived for each respiratory bin. The slice or volume data may be averaged over the entire volume or over a subset thereof, such as a region of interest. The averaging or other image processing may be implemented via a procedure having instructions written in a programming language, such as C++, Java, and C#, or written via MATLAB (The MathWorks, Inc., Natick, Mass.), or via other software or other computer-based procedures.

The average or other composite representations may then be stacked or ordered, per respiratory interval and, if applicable, slice location, to construct (or reconstruct) a time-resolved, volumetric data set. In some embodiments, an average 4D-MRI data set is constructed. The average 4D, or time-resolved, data set includes a number of volumetric data sets corresponding with the number of respiratory intervals defined in act 22. ("Average 4D-MRI"). In some cases, the average breathing cycle over the imaged duration may then be represented.

Acts 22, 24, and 26 of the method shown in FIG. 1 may be considered retrospective in nature, as the acts may be implemented after the scanning of act 20 (or other slice or volume data acquisition) is complete. For example, an image or image set may be constructed (or reconstructed) based on the previously captured slice or volume data and respiratory data. Alternatively or additionally, one or more of the remaining acts in the method may be implemented during the data acquisition, in which case the data may be processed in real-time. The remaining acts may be repeated or updated to take into account newly acquired slice or volume data. Further, it may be possible by way of mathematical comparison of the newest 2D or 3D frame or frames against the running average image, or and possibly in addition to analysis of the respiratory surrogate trace, to determine when a stable or robust average image has been rendered. The order of implementation of the acts of the method may thus vary from the example shown.

The 3D image constructed for each respiratory bin incorporates the data from all of the respiratory cycles of the slice or volume data acquisition session. By averaging over all available frames, per slice location and phase bin, the average 4D-MRI patient representation incorporates cycle-to-cycle variability during the prolonged imaging session. Averaging the data over multiple respiratory cycles may improve the signal-to-noise ratio (SNR) relative to the raw frames of slice or volume data.

Other combinations or processing of the slice or volume data over multiple respiratory data may derive other composite representations of the slice or volume data that also address the signal-to-noise ratio (SNR) and inter-cycle variability in respiration. Such processing may be an alternative or in addition to the averaging procedure described above. For example, the composite representation of the slice or volume data may be a maximum intensity projection (MIP) or minimum intensity projection (MinIP). In these embodiments, the slice or volume data for each respiratory phase is compared to derive the MIP and/or MinIP composite images, per respiratory interval. Other composite images may be derived from the slice or volume data based on discretized respiratory bins defined by the method of FIG. 1.

The methods described herein are not limited to the construction of various composite images based on temporal correlation or sorting of image data, as described in connection with the method of FIG. 1. Further or alternative processing of the slice or volume data may address anatomic variability present per respiratory phase. The methods described below include anatomic correlation and processing of the slice or volume data. The anatomic correlation and processing of the slice or volume data may reduce blurring in the composite images.

Figure 2:
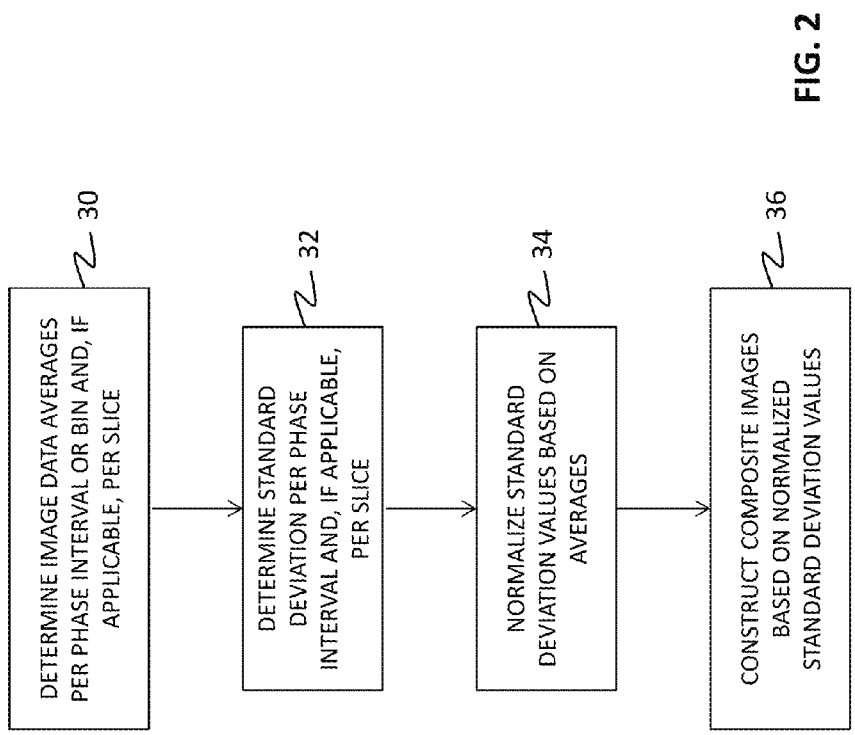
FIG. 2 is a flow diagram of an embodiment of a method of processing the volume data used to resolve respiratory motion and acquired by the imaging method of FIG. 1.

FIG. 2 depicts a number of image processing acts that may be implemented in connection with the slice or volume data and respiratory data acquisition acts described above. These acts may attempt to quantify cycle-to-cycle, or intra-respiratory interval, variability. These acts may be directed to reducing blurring in reconstructed or composite images. For example, these acts may be directed to addressing anatomic variability in the averaged composite 4D representation constructed as described above. The raw slice or volume data is already sorted and/or assigned retrospectively to respiratory intervals, or bins, as described above. In this embodiment, further image processing may begin in act 30 with a determination of the slice or volume data averages per respiratory interval or bin and, if applicable, per slice location. The averages may be determined as described above. In some embodiments, however, the averages need not be determined, or may be determined at a later point in the implementation of the method.

The sorted raw slice or volume data is used in act 32 to determine a standard deviation of the slice or volume data for each respiratory interval and, if applicable, each slice location. Images may then be derived from the standard deviation values. For example, respective 3D images may be constructed for each respiratory interval from the standard deviation values. For each slice (or volume) and respiratory interval in the 4D reconstruction of the slice or volume data, the raw slice or volume data of the frames may be used to determine the averages is also used to compute the standard deviation, or standard deviation 4D-MRI reconstruction. A high standard deviation value may be indicative of the pixels at that location having a relatively high amount of fluctuation from frame to frame. High standard deviation values may thus be indicative of variability or blurriness, which may result from being located near an anatomical edge or other gradient in the scanned volume.

In this embodiment, the standard deviation values may be normalized in act 34 before the image construction. The normalization of the pixel-wise standard deviation values may be based on the corresponding pixel-wise averages of the slice or volume data for each respiratory phase interval. For example, the standard deviation value may be expressed as a percentage of the nominal averaged value at each pixel location. If variability is present and the anatomy of interest has differing gray values from the surrounding anatomy, then the periphery of the anatomy of interest may present a high standard deviation, as shown in an image constructed in act 36 from the normalized standard deviation values. Such an image may provide a composite representation of the slice or volume data useful in radiotherapy planning for defining boundaries or enveloping regions per respiratory phase of the anatomic feature of interest (e.g., the tumor).

The standard deviation values may be determined from the set of voxel intensities and/or normalized as a percentage of the average value in a variety of ways. For instance, a threshold may be applied in some embodiments to suppress very low-signal or noisy portions of the image that would otherwise exhibit high normalized standard deviation values. Such thresholds may be useful in connection with imaging the lung surrounding a tumor. In one example, the normalized standard deviation value may be set to zero when the average 4D-MRI signal falls below the threshold.

The standard deviation images constructed in accordance with FIG. 2 may be combined with one or more other composite image reconstructions, such as MIP and/or MinIP images of the raw slice or volume data. Anatomic variability in the average 4D-MRI image representation may be resolved via these other composite image reconstructions, including the standard deviation 4D-MRI image representation. Each of these composite representations compiles the raw slice or volume data from multiple respiratory cycles, on a phase-by-phase basis.

Figure 3:
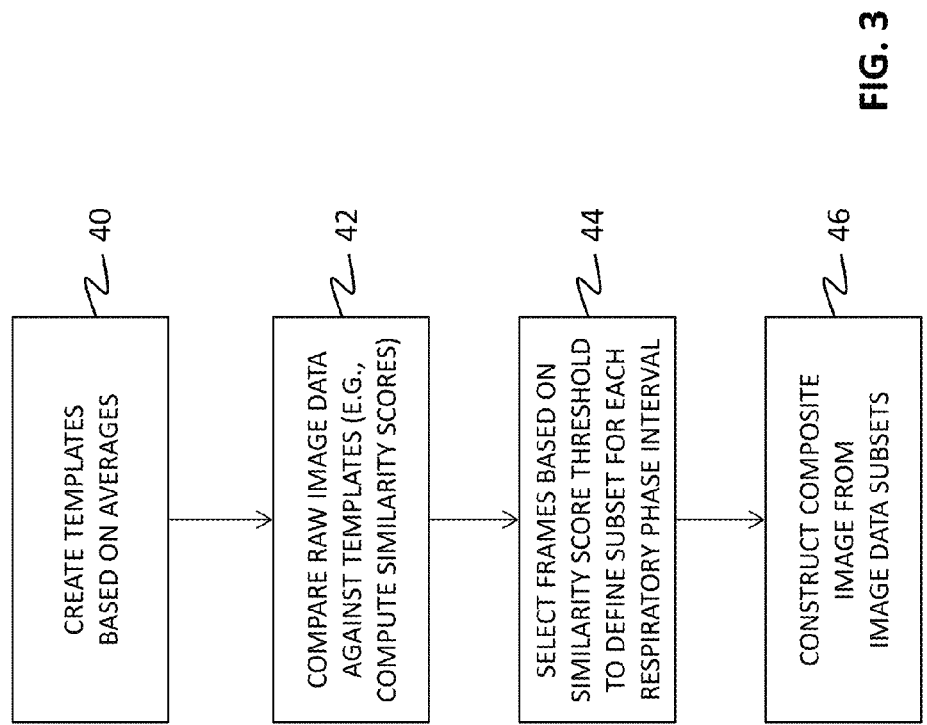
FIG. 3 is a flow diagram of an example method for resolving respiratory motion through further processing of the volume data acquired by the imaging method of FIG. 1.

FIG. 3 depicts further mage processing based on the slice or volume data averages determined as described above. Such further processing may include a second pass through the slice or volume data. In the second pass, the image processing may provide anatomy-based (or anatomic) correlation (or sorting) and processing of the raw slice or volume data to produce 4D representations. Such sorting uses the slice or volume data averages as a starting point for the second pass, or analysis, of the raw slice or volume data for each respiratory phase interval over all of the respiratory cycles in the imaging session. The second pass thus preserves the location information provided by the data averages, but potentially refines or improves the selection and/or number of frames used for averaging to improve the overall quality of image reconstruction. For example, anatomic sorting and processing may improve image contrast (e.g., reduce blurring). In this embodiment, the analysis may begin with the creation of image templates in act 40 based on the average 4D reconstruction. The creation of the image templates may correspond with the determination of the averages per phase bin and slice location, as described above. The 3D images that together make up the 4D reconstruction may serve as a set of templates.

With the averages in hand, the frames of raw slice or volume data are compared, e.g., per slice location, in act 42 against the image templates for each phase interval. Comparing the raw data against the reconstructed average 4D representation may include a computation of a similarity score between the raw data and the set of templates. For example, the similarity score may be determined by implementing one or more image registration procedures. Such procedures may compute a similarity metric for the raw image data in each respiratory phase interval. In some examples, the similarity metric is the normalized cross correlation. The nature of the image registration or template matching procedure or other comparison may vary. Other similarity measures that may be used in the comparison procedures include sum of squared differences (SSD), sum of absolute differences (SAD), mutual information, and various feature-based analysis techniques.

Given the similarity scores for each frame of slice or volume data, a subset of slice or volume data for each respiratory interval is selected in act 44. In some examples, the selection may be based on those data frames that meet a threshold of the similarity metric. Non-threshold selections may also be used. The similarity score per raw frame allows the subset of frames that best represents the anatomy at the desired position to be identified, as well as assigned for further image processing.

One or more composite representations of the slice or volume data may then be constructed in act 46 from the data subsets in each respiratory interval. For example, the composite representation may include an average of the slice or volume data subset. Averaging over the subset of frames may result in a 4D reconstruction with an improved signal-to-noise ratio (SNR) relative to that of a singular frame. Other composite representations (e.g., standard deviation, MIP, MinIP, etc.) may alternatively or additionally be constructed from the slice or volume data subsets. In each case, a further respective 3D image may be constructed for each respiratory phase interval based on the image data in each subset.

Acts 42 and 44 may be implemented on a portion of the slice or volume data, rather than the entire volume captured during the data acquisition. For example, a region of interest (ROI) may be selected before or concurrent with the comparison of the raw slice or volume data. The slice or volume data may thus be cropped or otherwise limited to one or more regions of interest. The image registration, template matching, or other comparison procedure may then be focused on a tumor region or other ROI. In the case of multiple template ROIs, a composite similarity score over the set of ROIs may be constructed as the basis of comparison.

In one example embodiment of the method of FIG. 3, each raw frame is compared with all template images for the corresponding slice location, i.e., one comparison for each template or reconstructed phase. The comparison may be limited to a user-selected ROI. For example, a normalized cross correlation score may be determined to find the respiratory bin of the average 4D representation that best matches each given raw frame. For example, if there exist ten reconstructed respiratory bins, then each raw frame has ten cross-correlation scores. The cross correlation or other similarity score for each comparison is stored. In cross-correlation-based comparisons, a score of unity means that the template image matches the raw frame perfectly. Otherwise, the score is less than unity. The best matching template (highest score) may determine the new respiratory interval for that particular raw image, regardless of which frame it had been assigned to in the first-pass (respiratory trace-based) sorting. In one example, if $A_{ij}$ is the $i^{th}$ raw image belonging to the $j^{th}$ respiratory interval and $A_j$ is the representative average image for the $j^{th}$ respiratory interval, then, for each $A_{ij}$, a normalized cross-correlation is computed between $A_{ij}$ and $A_j$. With, for example, ten respiratory intervals, for a given $A_{ij}$, ten computed normalized cross correlation values are thusly determined. $A_{ij}$ may therefore be re-assigned to the respiratory interval whose representative image, $A_j$, resulted in the highest normalized cross correlation with $A_{ij}$.

In this example, rather than compute the cross-correlation over the entire field of view (FOV), a rectangular region-of-interest (ROI) is selected by a user looking interactively at an image formed from the slice or volume data. For example, the user may analyze a maximum intensity projection (MIP) rendering of the average 4D representation (e.g., a MIP over all respiratory bins) to assure that the ROI covers the object or tumor of interest over all respiratory intervals. The cropped ROI(s) is defined to contain the anatomy of interest (e.g., a tumor with surrounding vasculature). In some embodiments, for slice-to-slice volume consistency, the same ROI is used for all slices, although more than one ROI may be used. The normalized cross-correlation value for the ROI from the given raw frame ($I_k$) compared against the template ROI for the given respiratory phase at that slice location ($I_N$) may then be determined as follows:

$$cc_{k,N} = \Sigma_{i,j}(I_k \cdot I_N)/\sqrt{\{\Sigma_{i,j}(I_k \cdot I_k) \times \Sigma_{i,j}(I_N \cdot I_N)\}},$$

where the summation, $\Sigma_{i,j}$, runs over the pixel indices of the cropped ROIs. From the newly-sorted set of available frames per slice location and respiratory interval, the best matching frames (e.g., with the highest normalized cross correlation score) for the respiratory intervals are then selected for averaging to produce an improved 4D image reconstruction.

Figure 4:
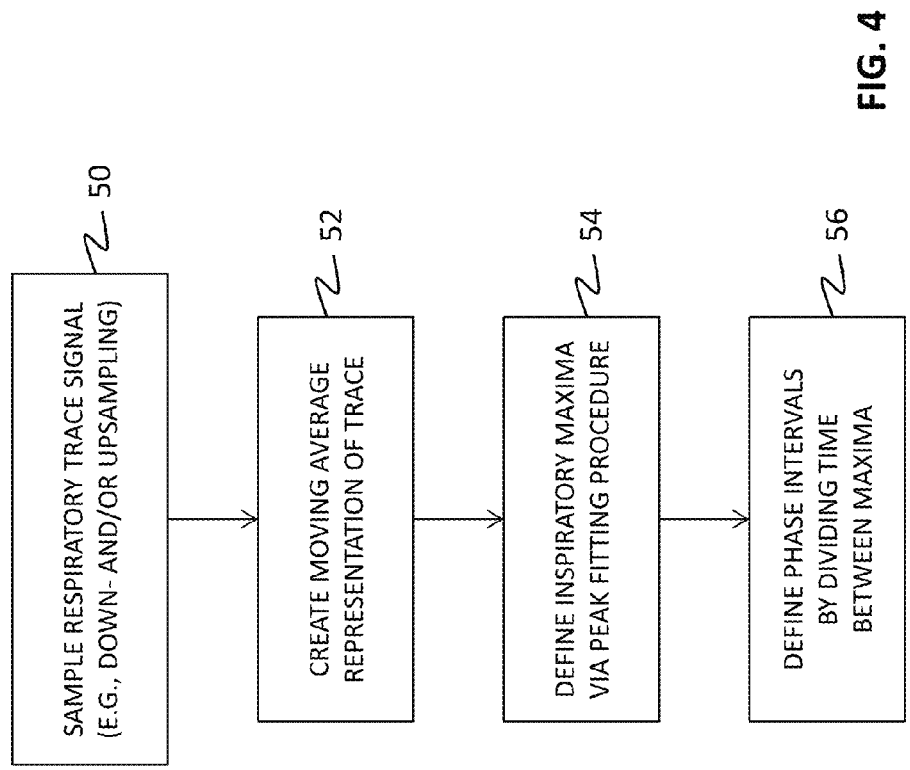
FIG. 4 is a flow diagram of a respiratory signal processing method in accordance with one embodiment.

FIG. 4 depicts the processing of respiratory data in accordance with on embodiment. The respiratory signal provided by the belt or other respiration monitor may be processed in preparation for defining and dividing each respiratory cycle and, thus, defining the respiratory intervals per cycle. In this embodiment, the respiratory cycles are defined by identifying the inspiratory maxima with the aid of a moving average representation of the sampled external respiratory signal. The set of respiratory intervals in each cycle may then be defined by dividing the time between each peak inspiratory maximum into equal-time intervals. Other techniques to segment the surrogate respiratory trace to generate a representation of an average breathing cycle may be used.

The processing of the respiratory signal may include one or more sampling procedures. In this example, noise is reduced in act 50 by down-sampling or more coarsely averaging and/or up-sampling the trace or signal to preserve the raw temporal resolution. After the respiratory signal is re-sampled or more coarsely averaged, the sampled data may be smoothed using, for instance, a cubic spline interpolation for each step. The average respiratory frequency over the imaging session may be determined by finding the peak in the power spectrum resulting from a fast Fourier transform of the smoothed or raw data. A moving average representation of the respiratory data trace or signal (MAT) may be determined in act 52 by integration of the smoothed data over one or more respiratory periods (or portions thereof). The MAT representation may be useful in subsequent processing of the respiratory data by helping to define respiratory peaks and valleys. Further details regarding the MAT determination are set forth in Lu et al., "A semi-automatic method for peak and valley detection in free-breathing respiratory waveforms," Med Phys. 33, 3634-3636 (2006), the entire disclosure of which is hereby incorporated by reference. In some embodiments, portions of the breathing trace or data, RT(t), greater than the MAT representation are considered, using, for example, a Gaussian peak fitting method, to determine the peak inspiratory maxima or "trigger" points. Other portions of the signal, and other peak fitting or other procedures, may be used to define the inspiratory maxima. In one example, the end-exhale minima portions of the respiratory cycle are not incorporated into this procedure of the image processing method in view of interference at those times from cardiac noise. Such interference is often times clearly discernable in the exhale portions of the cycle. A discretized representation of the respiratory phase, RP(t), is then determined in act 56 for all times between a given trigger point and the subsequent trigger point by dividing the number of available time samples into equal-time-weighted bins ($N_{bins}$), thereby defining respiratory intervals.

Figure 5:
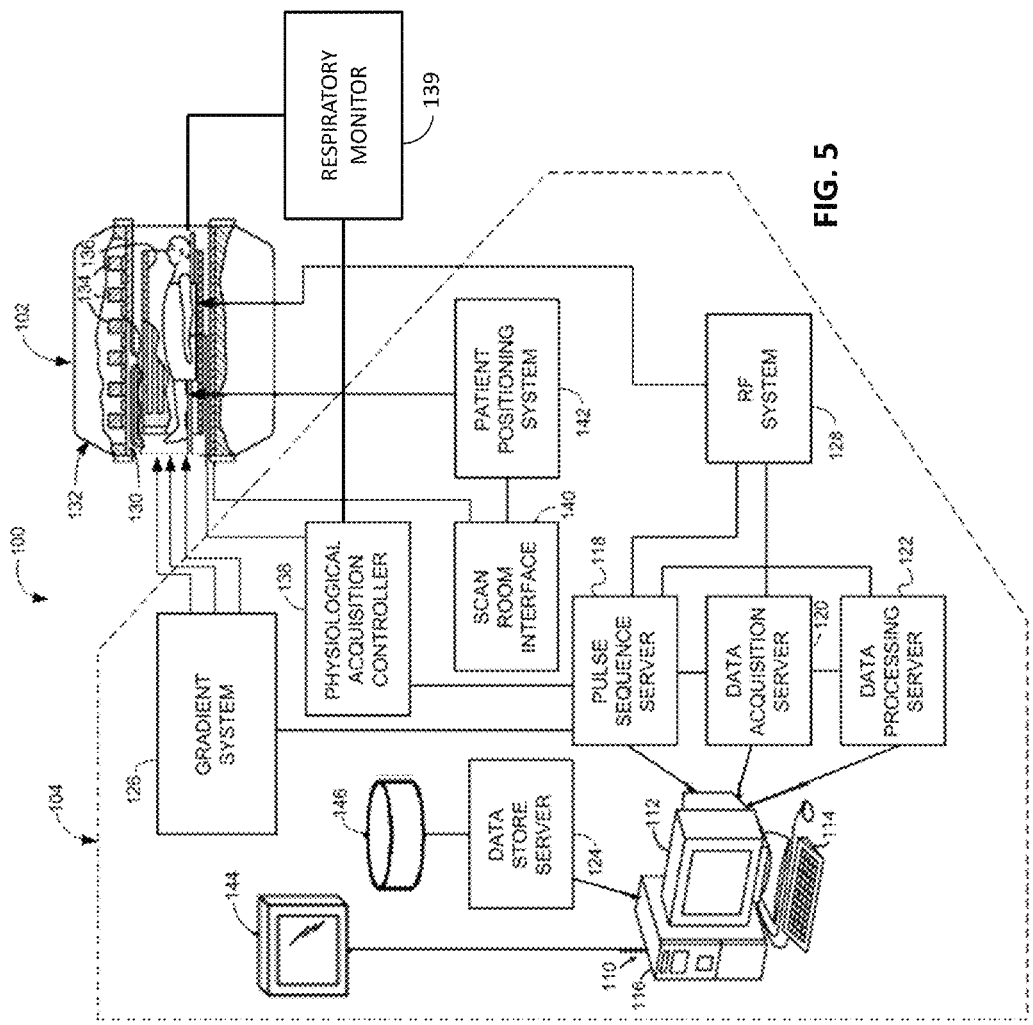
FIG. 5 is a block diagram of an example embodiment of a magnetic resonance imaging (MRI) system configured to implement imaging for resolving respiratory motion.

FIG. 5 depicts a magnetic resonance imaging ("MRI") system 100 for dynamic volumetric imaging and resolving respiratory motion in accordance with one embodiment. The MRI system 100 generally includes a scanner or data acquisition unit 102 and a controller or control system 104 for directing the operation of the scanner 102. The scanner 102 acquires slice or volume data over a plurality of respiratory cycles. The scanner 102 may be configured to capture 2D frames (e.g., image slices) or 3D or volumetric frames. The slice or volume data may thus be arranged in a plurality of 2D or 3D slice or volume frames. The scanner 102 is in communication with the control system 104 so that the control system 104 can direct the scanner 102 to implement a series of pulse sequences configured to generate the 2D or 3D images.

The control system 104 includes a workstation 110 having one or more output interfaces (e.g., display) 112 and one or more input interfaces (e.g., keyboard) 114. The workstation 110 includes a processor 116, which may be a commercially available, programmable machine running a commercially available operating system. The workstation 110 provides an operator interface that enables scan sequences to be entered into or otherwise defined for the control system 104 and the MRI system 100. The workstation 110 may be coupled to a number of servers or other processors, including, in this example, a pulse sequence server 118, a data acquisition server 120, a data processing server 122, and a data store server 124, each of which may include one or more processors configured to implement one or more acts or other aspects of the image correlation and processing methods. The workstation 110 and the servers 118, 120, 122 and 124 may communicate with each other via any desired communication technique, protocol, or standard. The components of the control system 104 may be coupled to one another via a data bus or network (not shown) and need not be connected via respective, dedicated communication lines as shown. Any one or more of the components of the control system 104 may be implemented as a service unit, module, or other unit implemented by a common physical machine or other device. Additional, different, or fewer components may be provided, such as combining two or more servers or providing the workstation functionality on a server or vice versa. For example, one or more of the servers 120, 122, 124 may share one or more processors.

The processor 116 and/or one or more of the processors of the servers 120, 122, 124 may be configured to divide each respiratory cycle of the plurality of respiratory cycles into a set of respiratory phase intervals, as described above. One or more of these processors may also be configured to resolve the 4D composite representations of the slice or volume data by constructing respective composite 3D images for the respiratory phase intervals, as described above. The construction may be based on 2D frames (e.g., image slices) or 3D frames acquired during the respiratory phase interval from each respiratory cycle of the plurality of respiratory cycles, as described above. The image construction, image correlation and other image processing described above may be implemented by one or more of these processors.

In some example embodiments, the system 100 may implement a two-phase image acquisition method. The first phase is the excitation phase, in which a magnetic resonance signal is created in the subject. To that end, the body being examined is subjected to a main magnetic field, $B_0$, to align the individual magnetic moments, or spins, of the nuclei in the tissue with the axis of the polarizing field (conventionally, the z-axis). The main magnetic field also causes the magnetic moments to resonantly precess about the axis at their characteristic Larmor frequency. If the tissue is then subjected to a radio frequency (RF) excitation pulse, $B_1$, with a frequency near the Larmor frequency, a magnetic field in the x-y plane re-orients, flips, or tips the net aligned moment, $M_z$, into or toward the x-y plane, producing a net transverse magnetic moment $M_{xy}$, the so-called spin magnetization. The second phase is the acquisition phase, in which the system 100 receives an electromagnetic signal emitted as the excited nuclei relax back into alignment with the z-axis after the excitation pulse $B_1$ is terminated. These two phases are repeated pair-wise to acquire enough data to construct an image.

The excitation phase may be tailored to localize the excitation pulse to a specific region within the subject, such as a 3D slab or a relatively thin 2D slice. The subsequent acquisition may encode the localized region in all three dimensions for a 3D slab or only in-plane for a thin slice. The region to be imaged may be scanned by a sequence of measurement cycles in which magnetic field gradients ($G_x$, $G_y$, and $G_z$) vary according to the particular localization method being used. Tailored RF pulses may also be used to localize the excitations.

The MR signals acquired with the system 100 are signal samples of the subject of the examination in Fourier space, or what is often referred to in the art as "k-space." Each MR measurement cycle, or pulse sequence, may sample a portion of k-space along a sampling trajectory characteristic of that pulse sequence. The pulse sequences may sample k-space in a raster scan-like pattern sometimes referred to as a "spin-warp", a "Fourier", a "rectilinear", or a "Cartesian" scan. The spin-warp scan technique employs a variable amplitude phase encoding magnetic field gradient pulse prior to the acquisition of MR spin-echo signals to phase encode spatial information in the direction of this gradient. In a 2D implementation ("2DFT"), for example, spatial information is encoded in one direction by applying a phase encoding gradient, $G_y$, along that direction, and then a spin-echo signal is acquired in the presence of a readout magnetic field gradient, $G_x$, in a direction orthogonal to the phase encoding direction. The readout gradient present during the spin-echo acquisition encodes spatial information in the orthogonal direction. In the 2DFT pulse sequence, the magnitude of the phase encoding gradient pulse, $G_y$, may be incremented, $\Delta G_y$, in the sequence of measurement cycles, or "views" that are acquired during the scan to produce a set of k-space MR data from which an entire image can be reconstructed.

In the example embodiment shown in FIG. 5, the pulse sequence server 118 functions in response to instructions downloaded from the workstation 110 to operate a gradient system 126 and a radio frequency ("RF") system 128. Gradient waveforms to perform the prescribed scan are produced and applied to the gradient system 126 that excites gradient coils in a gradient coil assembly 130 to produce the magnetic field gradients $G_x$, $G_y$, and $G_z$ used for position-encoding MR signals. The gradient coil assembly 130 forms part of a magnet assembly 132 that includes an annular or other polarizing magnet 134 and a whole-body RF coil array 136. In some cases, the whole-body RF coil array 136 is constructed in the form of a so-called birdcage antenna and has a number of individual antenna rods which run parallel to the patient tunnel and uniformly distributed in a circumferential arrangement around the patient tunnel. The individual antenna rods may be capacitively coupled to one another in a ring shape at one end of the birdcage antenna.

RF excitation waveforms are applied to the RF coil 136 by the RF system 128 to perform a selected magnetic resonance pulse sequence. Responsive MR signals detected by the RF coil 136 or a separate local coil (not shown) are received by the RF system 128, amplified, demodulated, filtered and digitized under direction of the pulse sequence server 118. The RF system 128 includes an RF transmitter for producing a wide variety of RF pulses used in MR pulse sequences. The RF transmitter is responsive to the selected scan sequence and direction from the pulse sequence server 118 to produce RF pulses of the desired frequency, phase and pulse amplitude waveform. The generated RF pulses may be applied to the whole body RF coil 136 or to one or more local coils or coil arrays. As described below, the RF transmitter includes a plurality of transmission channels to produce RF pulses formed via the superimposition of the RF pulses generated by each transmission channel.

The RF system 128 also includes one or more RF receiver channels. Each RF receiver channel includes an RF amplifier that amplifies the MR signal received by the coil to which it is connected. Each receiver may also include a detector that collects and digitizes in-phase (I) and quadrature (Q) components of the received MR signal.

The pulse sequence server 118 may receive patient data from a physiological acquisition controller 138. The controller 138 receives signals from a number of different sensors connected to the patient, such as ECG signals from electrodes or respiratory signals from a respiratory monitor 139 of the system 100. The respiratory monitor 139 may include a pneumatic belt, IR sensor or camera, or other type of sensor for acquiring a surrogate or representation of the respiration of the subject. One or more other respiratory monitors, such as a bellows, may also be used by the system 100 to generate signals indicative of respiration. Such signals may be used by the pulse sequence server 118 to synchronize, or trigger, the initiation of the scan sequence with the subject's respiration and/or heartbeat. The scan sequence may be stopped using such signals in, for instance, an example embodiment that acquires data until a certain number of samples are acquired. In one example, the physiological acquisition controller 138 includes a physiological monitoring or measurement unit (PMU).

The respiratory monitor 139 is configured to acquire respiratory surrogate data over a plurality of respiratory cycles. One or more of the processors of the control system 104 is in communication with the respiratory monitor 139 and the scanner 102 to implement the methods described above. For instance, one or more processors may be configured to divide each respiratory cycle of the plurality of respiratory cycles into a set of respiratory phase intervals based on the respiratory surrogate data. A respective composite 3D image may then be constructed for each respiratory phase interval based on the image frames acquired during the respiratory phase interval from each respiratory cycle of the plurality of respiratory cycles.

The pulse sequence server 118 also connects to a scan room interface circuit 140 that receives signals from various sensors associated with the condition of the patient or subject and the magnet system. It is also through the scan room interface circuit 140 that a subject positioning system 142 receives commands to move the subject to desired positions during the scan sequence. The subject positioning system 142 may direct one or more motors (not shown) that drive a bed and, thus, the subject, to a desired position.

The digitized MR signal samples produced by the RF system 128 are received by the data acquisition server 120. The data acquisition server 120 operates in response to instructions downloaded from the workstation 110 to receive the real-time MR data and provide buffer storage such that no data is lost by data overrun. In some scan sequences, the data acquisition server 120 passes the acquired MR data to the data processor server 122. However, in scans that require information derived from acquired MR data to control the further performance of the scan, the data acquisition server 120 may be programmed to produce such information and convey it to the pulse sequence server 118. For example, during calibration or other pre-scans, MR data is acquired and used to calibrate the pulse sequence performed by the pulse sequence server 118. The calibration data may be stored in a memory or storage device or other unit of, associated with, or in communication with, any of the aforementioned servers or other devices. Also, navigator signals may be acquired during a scan and used to adjust RF or gradient system operating parameters or to control the view order in which k-space is sampled. The data acquisition server 120 may be employed to process MR signals used to detect the arrival of contrast agent in a magnetic resonance angiography (MRA) scan. In all these examples, the data acquisition server 120 acquires MR data and processes it in real-time to produce information that is used to control the scan.

The data processing server 122 receives MR data from the data acquisition server 120 and processes the MR data in accordance with instructions downloaded from the workstation 110. Such processing may include, for example, Fourier transformation of raw k-space MR data to produce two or 3D images, the application of filters to a reconstructed image, the performance of back-projection image reconstruction of acquired MR data, the calculation of functional MR images, the calculation of motion or flow images, segmentation, or other visualization processes.

Images reconstructed by the data processing server 122 are conveyed back to the workstation 110 for storage. Real-time images may be stored in a database memory cache (not shown) from which they may be output to the display 112 or an auxiliary terminal or console 144, which may be located near the magnet assembly 132 for use by attending physicians or other operators. Batch mode images or selected real time images are stored in a database on mass storage device 146, which may include any desired storage medium. When such images have been reconstructed and transferred to storage, the data processing server 122 notifies the data store server 124 on the workstation 110. The workstation 110 may be used by an operator to archive the images, produce films, or send the images via a network to other facilities.

The data processing server 122 may also or alternatively be configured to process the image data and respiratory data in accordance with the methods described above.

Figure 6:
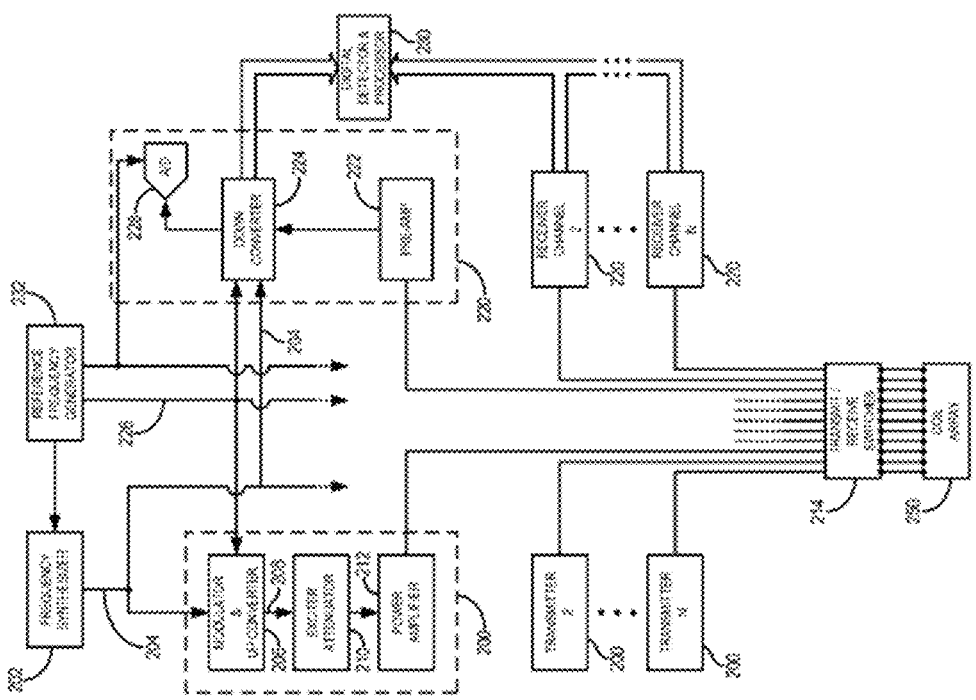
FIG. 6 is a block diagram of an RF system and other components of the MRI system of FIG. 5.

Referring now to FIG. 6, one example of the RF system 128 and other components of the system 100 is shown in greater detail. The whole body coil array 136 may include a plurality of coil elements that can be separately driven by a plurality of RF transmitters 200 to produce a desired RF field-of-excitation ("FOX"). Each RF transmitter 200 forms one of the array of channels that, when superimposed, collectively define the composite RF signal. The coil array 136 may also be used with a plurality of receive channels 202. Alternatively or additionally, another whole body RF coil array (not shown) or another local RF coil may be used to acquire the MR signals. A variety of different coil array structures may be used as part of the system 100 (FIG. 5).

The RF system 126 includes a set of transmitters 200, each of which produces an individual, selected RF excitation field. The base, or carrier, frequency of this RF excitation field is produced under control of a frequency synthesizer 204, which receives a set of digital control signals from the pulse sequence server 118. These control signals may include data representative of the frequency and phase of the RF carrier signal, which may be produced at an output 206, The RF carrier is applied to a modulator and up converter 208 in each transmitter 200, where the RF carrier amplitude is modulated in response to a signal also received from the pulse sequence server 118. The signal defines the envelope of the RF excitation pulse to be produced and is generated by sequentially reading out a series of stored digital values. These stored digital values may, be changed to enable any desired RF pulse envelope to be produced by each transmitter 200.

The magnitude of the RF excitation pulse produced at an output 210 is attenuated by an exciter attenuator circuit 212 in each transmitter 200. Each attenuator circuit 212 receives a digital command from the pulse sequence server 118. The attenuated RF excitation pulses are applied to a power amplifier 214 in each transmitter 200. The power amplifiers are current source devices that connect to respective transmit inputs on a set of transmit/receive switches 216. In this example, a desired number N of the transmitters 200 are employed and connected through a corresponding number N of the transmit/receive switches 216 to a corresponding number N of the coil elements in the RF coil array 136.

The signal produced by the subject is picked up by the coil array 200 and applied to the inputs of the set of receive channels 202. A pre-amplifier 218 in each receiver channel 202 amplifies the signal by an amount determined by a digital attenuation signal received from the pulse sequence server 118 (FIG. 5). The received signal is at or around the Larmor frequency, and this high frequency signal is down converted in a two-step process by a down converter 220, which first mixes the NMR signal with the carrier signal on the line 206, and then mixes the resulting difference signal with a reference signal on a line 222. The down converter NMR signal is applied to the input of an analog-to-digital ("A/D") converter 224 which samples and digitizes the analog signal and applies it to a digital detector and signal processor 226, which produces 16-bit in-phase (I) values and 16-bit quadrature (Q) values corresponding to the received signal. The resulting stream of digitized I and Q values of the received signal are output to the data acquisition server 120 (FIG. 5). The reference signal as well as the sampling signal applied to the A/D converter 224 are produced by a reference frequency generator 228.

The transmit/receive switches 216 are controlled and directed by the pulse sequence server 118 (FIG. 5) to connect the N transmitters 200 to the N coil elements in the coil array 136 during those parts of the pulse sequence in which an RF field is to be produced. Each transmitter 200 is separately controlled by the pulse sequence server 118 (FIG. 5) to produce an RF field of a desired amplitude, frequency, phase, and envelope at each of the N coil elements. The combined RF fields of the N coil elements produce the prescribed $B_1$ field throughout the region of interest in the subject during the imaging phase of the procedure.

When the $B_1$ field is not produced, the pulse sequence server 118 directs the transmit/receive switches 216 to connect each of the N receive channels to the respective N coil elements. Signals produced by the excited spins in the subject are picked up and separately processed as described above.

Figure 7:
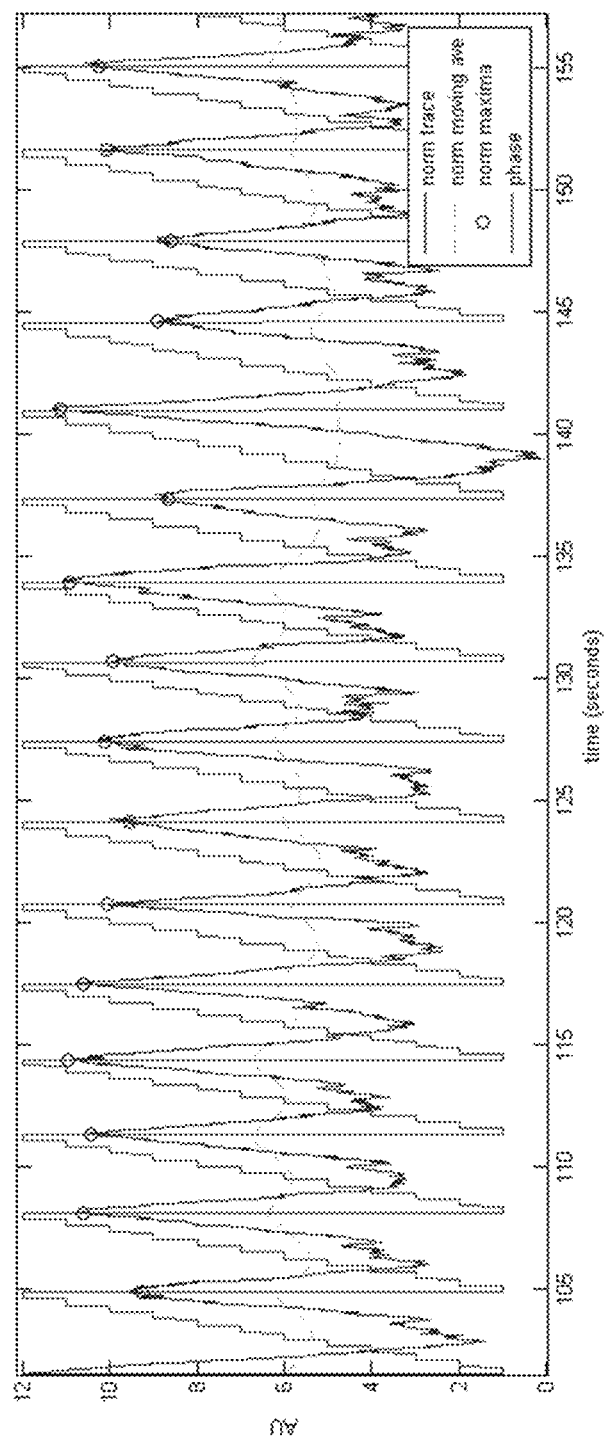
FIG. 7 is a graphical plot of a sample respiratory signal along with respiratory parameters generated from the respiratory signal in accordance with one embodiment.

FIG. 7 depicts a portion of a respiratory signal acquired via the respiratory monitor 139. The respiratory signal is acquired simultaneously with imaging, the details of which are described below. A pneumatic belt (Siemens AG, Erlangen, Germany) is wrapped around the thorax or abdomen of the subject to provide the respiratory signal. A physiological monitoring control interface (PMU) may be used to encode the respiratory data in ASCII format at 50 Hz, synchronous with image acquisition. For TrueFISP acquisitions the same clock may provide the time stamp in the image data for the 2D frames.

FIG. 7 also depicts the processing of the respiratory data into 12 respiratory phase intervals or bins in accordance with the above-described methods. In this example, the raw respiratory signal is sampled and used to determine a moving average trace or signal, MAT(t), shown as the dot-dashed line. Peak locations, or "trigger" points, are then determined from the moving average signal, as indicated by circles. A higher-frequency component of the respiratory signal arising from cardiac interference may be seen around the exhale portions of the respiratory cycles. In some examples, the above-described sorting methods may be used to resolve or decouple respiratory-based motion from heart motion. The 12 phase intervals are then defined between successive trigger points, each phase interval being shown as a discrete step in each respiratory cycle.

In one embodiment, the synchronous MR imaging is performed with a Siemens MAGNETOM Espree 1.5 T (Siemens AG, Erlangen, Germany). A single Body Matrix coil (Siemens AG, Erlangen, Germany) is wrapped over the volunteers' thorax. 2D TrueFISP is used to acquire sequential sagittal and coronal slices through a 3D lung volume. The sequential (or slice-stepping) acquisition may help preserve inter-slice volume consistency over the imaging duration, insofar as systematic movement (e.g., muscle relaxation) of the subject is captured equally per slice location. Sagittal and coronal planes may minimize out-of-plane motion of vascular anatomy. The in-plane pixel resolution is 2 mm$^2$ with a slice thickness of 5 mm. The center positions of the slices may be spaced 2.5 mm to 5 mm apart. Parameters such as FOV, flip angle, and TE are adjusted to provide 2D frame (repetition) rates of 3.3-3.4 Hz.

In one example, a subject is imaged continuously for approximately 10 minutes in the sagittal orientation with an acquisition matrix of 120 (AP)×160 (SI) with 10 slices covering 2.5 cm laterally (flip angle=65°; TE=1.53 ms, and frame rate=298 ms). In a second example, a subject is imaged in both the sagittal and coronal orientations over approximately 30 minutes. The sagittal acquisition matrix is 120 (AP)×160 (SI) and 20 slices are acquired covering 5 cm laterally (flip angle=70°; TE=1.37 ms, and frame rate=268 ms). The coronal acquisition matrix is 160 (LAT)×160 (SI) and 20 slices are acquired over 5 cm anterio-posteriorly (flip angle=70°; TE=1.3 ms, and frame rate=290 ms).

3D distortion corrections are applied by the Siemens Syngo workstation (Siemens AG, Erlangen, Germany) to the raw 2D images acquired for the second example. Such corrections may be useful for geometric integrity and radiotherapy planning.

In these examples, the average and standard deviation 4D-MRI datasets are constructed as described above.

Figure 8:
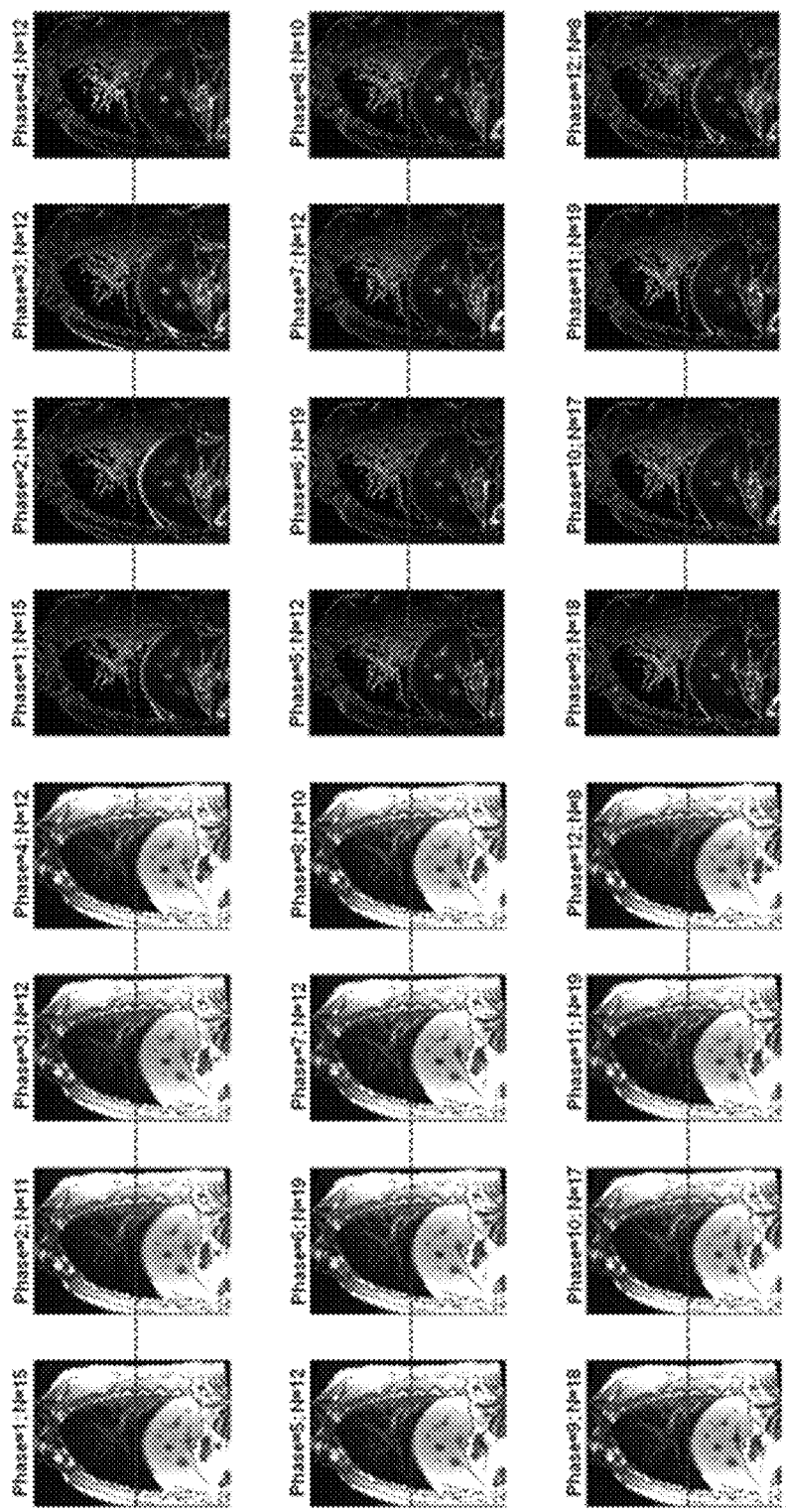
FIG. 8 depicts medical image representations of a set of reconstructed MRI slice images for a number of respiratory phase intervals in accordance with one embodiment

FIG. 8 depicts the datasets for slice location 5 of 10 for the subject in the first example with 12 phase bins. The left panel shows the average 4D-MRI reconstruction and the right panel shows the standard deviation 4D-MRI reconstruction. The diaphragm location at end exhale is shown as a dashed red line for reference. The lung-diaphragm interface, for example, yields a brighter standard deviation image around inhale than around exhale given more anatomic variability in these phases.

Figure 9:
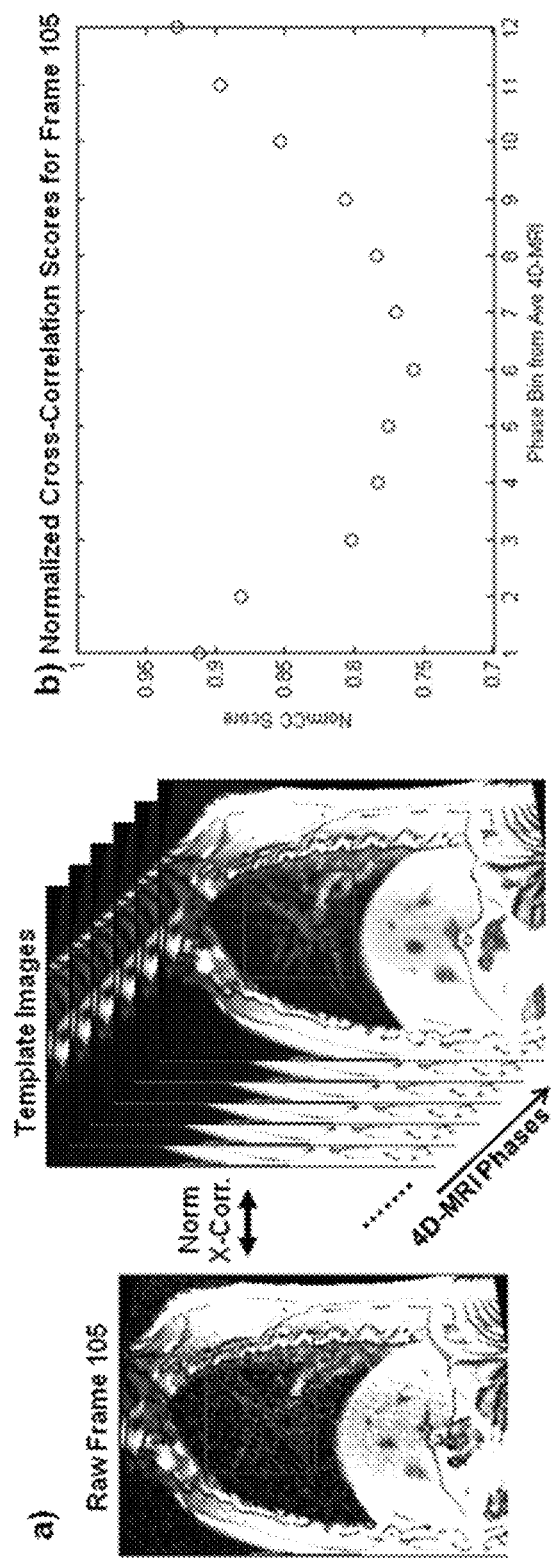
FIG. 9 depicts medical image representations and a graphical plot of the further processing of the volume data in accordance with the example method of FIG. 3.

FIG. 9 depicts an example of the second stage of averaging or processing for slice location 5 of 10 for the subject in the first example over the 12 phase bins for a randomly selected raw frame (#105). Raw frames are compared against the set of average 4D-MRI images for the corresponding slice location using a normalized cross correlation metric computed within a user-selected region of interest (ROI). Despite noise in the raw images, the metric provides a robust indication of the best matching phase bin (phase 12 in this case, which happened to be the same phase bin selected in the first pass). The comparison of the normalized cross-correlation value for the ROI for the frame #105 against a template ROI (e.g., the average image data) is shown in the graphical plot of FIG. 9. Note that despite low SNR in the individual frames, the normalized cross correlation provides a clear indication of the best match. Implementation of the cross-correlation metric comparison may be aided in the thorax if the lung/diaphragm interface is not included in the ROI. The higher signal from portions below the diaphragm may bias the scoring towards the selection of frames with less lung in the ROI (e.g., during exhalation). The comparison may be then extended throughout the dataset. From the newly-sorted set of available frames per slice location and phase bin, the best matching frames (with the highest normalized cross correlation score) were selected for averaging to produce an improved 4D-MRI representation.

Figure 10:
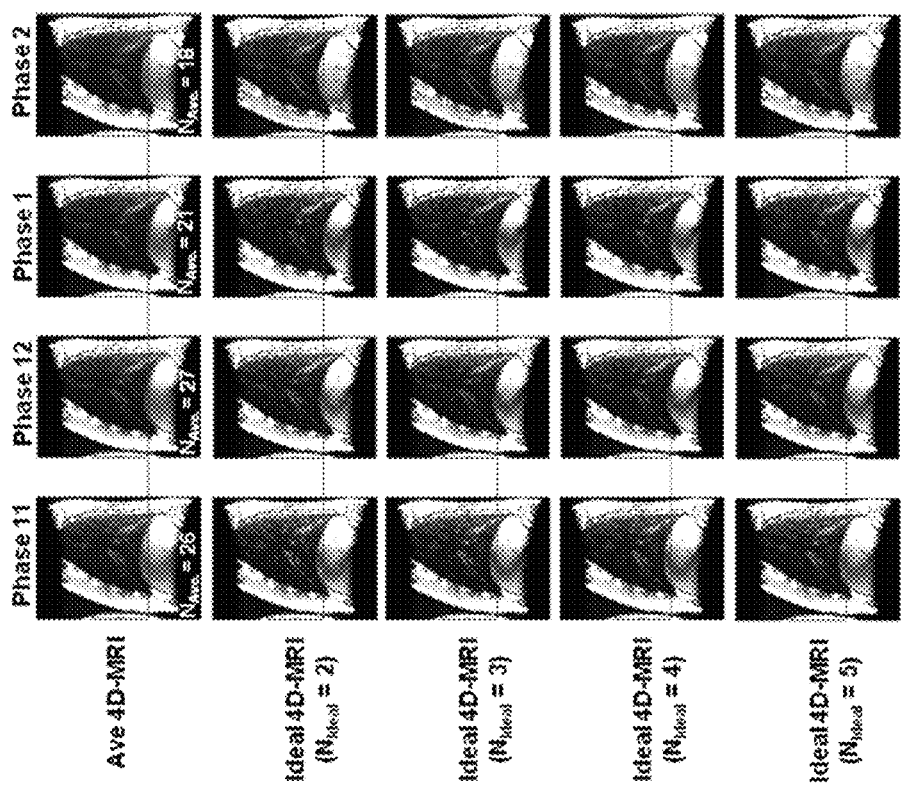
FIGS. 10 and 11 depict medical image representations of multiple sets of reconstructed MRI slice images for a number of respiratory phase intervals, the multiple sets comparing reconstructions generated in accordance with the example methods of FIGS. 1 and 3.

FIG. 10 depicts the results for the sagittal study of the subject in the second example. The top row shows the average 4D-MRI representation for four phases around inhale resulting from a 12-phase reconstruction for a particular slice location (18/20). The number N of frames producing these averages is given in each case. The vascular anatomy in the images is noticeably blurred, especially phases 12 and 2. The result of the improved 4D-MRI reconstructions for different numbers of best matching frames ($N_1$) are shown in the remaining rows. Image contrast improvements are evident in the second-pass results. Whereas it is difficult for the eye to distinguish SNR improvements comparing the reconstructions for, e.g., $N_1=2$ vs. $N_1=3$, differences are noticed comparing $N_1=2$ vs. $N_1=5$. Each of these rows depicts the results for the noted phases. The most inferior diaphragm dome location (taken from phase 1 of the average 4D-MRI representation) is shown for reference via a dotted line.

Figure 11:
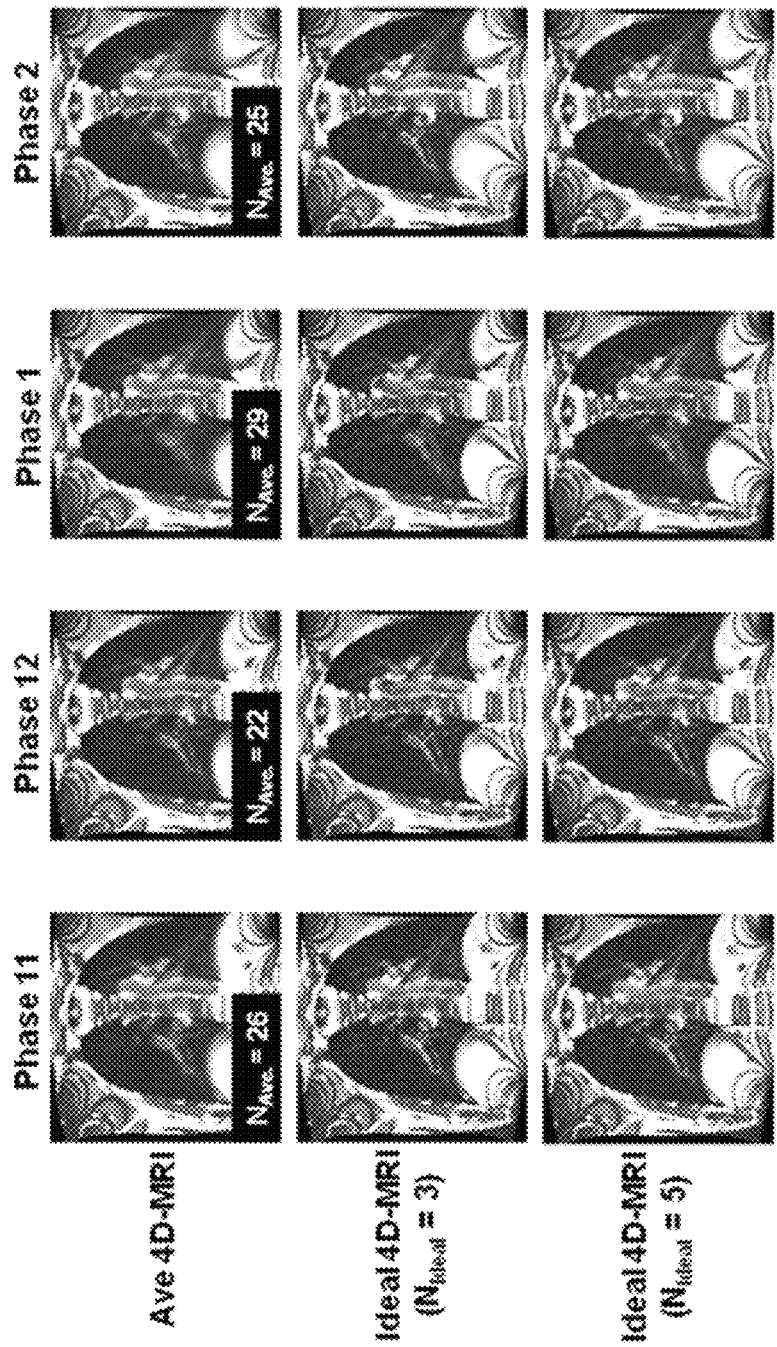

FIG. 11 depicts the second-pass, improved 4D-MRI reconstructions for slice 18 of 20 for the coronal series for the subject in the second example in a 12-phase reconstruction. The top row shows the average 4D-MRI for 4 phases around inhale. The number N of images producing these averages is given in each case. The second and third rows show the improved 4D-MRI reconstructions for $N_1=3$ and 5, respectively, for the same 4 phases. The ROI for the normalized cross-correlation comparison is shown on all images for reference. Sharpening is improved in the four selected phases around inhale. As evidenced by the improved 4D-MRI result for phase 1, the extent to which the improved 4D-MRI improves contrast may depend on the availability of frames with anatomy of interest (in the ROI) at the average 4D-MRI location. This likelihood may increase with imaging duration and/or by decreasing the number of phase bins used in the reconstructions. The latter technique may present a tradeoff, insofar as decreasing the number of phase bins may produce a blurrier average 4D-MRI reconstruction.

The methods and systems described above may be used to provide clean images at each respiratory phase or for each respiratory interval, such that accurate segmentations (manual or automatic) may be performed to define treatment volumes. The methods and systems may also support acquisition of 4D information that characterizes an individual patient's respiratory tumor motion. In cases of direct 3D image acquisition, a 3D probability density function (PDF) plot or other similar representation of the displacement of continuously monitored tumor motion may be generated. Such representations may be used in radiation therapy planning for a specific patient (for example: indirectly, to determine whether a given trial plan is robust to the observed motion; or, directly: to aid a priori in definition of the radiation beam portals and associated 2D radiation intensity patterns) or may provide a metric for discerning reproducibility or stability of breathing motion in the context of serial imaging.

The methods and systems described above may be used to provide robust, respiratory interval-dependent internal target margins for radiotherapy. The methods and systems may be configured for applications involving interval-to-interval deformable image registration (e.g., for automated anatomic image segmentation).

While the invention has been described above by reference to various embodiments, it should be understood that many changes and modifications may be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method of dynamic imaging, the method comprising:
   acquiring volume data for a volume of a patient over a plurality of respiratory cycles;
   acquiring respiratory data representative of respiration over the plurality of respiratory cycles;
   dividing each respiratory cycle of the plurality of respiratory cycles into a set of respiratory intervals based on the respiratory data;
   correlating the volume data produced over the plurality of respiratory cycles with a respective respiratory interval of the set of respiratory intervals;
   determining average volume data for the volume per respiratory interval based on the volume data from the plurality of respiratory cycles correlated with the respective respiratory interval;
   selecting, for each respiratory interval, a subset of the volume data correlated with the respective respiratory interval, using the average volume data for the respective respiratory interval as a template; and
   displaying a respective composite three-dimensional image of the volume for each respiratory interval based on the selected subset of the volume data for each respiratory interval.

2. The method of claim 1, wherein displaying the respective composite three-dimensional image comprises determining a standard deviation of the volume data for each respiratory interval.

3. The method of claim 2, further comprising normalizing the standard deviation based on the average volume data for each respiratory interval.

4. The method of claim 1, wherein displaying the respective composite three-dimensional image comprises determining a maximum or minimum intensity projection of the volume data for each respiratory interval.

5. The method of claim 1, further comprising:
   computing a similarity metric for the volume data in each respiratory interval from each respiratory cycle of the plurality of respiratory cycles relative to the average volume data for the respiratory interval;
   wherein selecting the subset comprises determining, for each respiratory interval, a subset of images of the volume data that meet a threshold of the similarity metric; and
   wherein displaying the respective composite three-dimensional image comprises displaying a further respective three-dimensional image for each respiratory interval based on an average of the volume data in each subset.

6. The method of claim 5, wherein computing the similarity metric comprises cropping the volume data to one or more regions of interest.

7. The method of claim 5, wherein the similarity metric is normalized cross correlation.

8. The method of claim 1, wherein the volume data comprises two-dimensional magnetic resonance imaging (MRI) images for a plurality of slice locations that collectively form the volume.

9. The method of claim 1, wherein acquiring the respiratory data comprises acquiring and sampling an external respiratory surrogate signal.

10. The method of claim 9, wherein dividing each respiratory cycle comprises:
    defining each respiratory cycle based on peak inspiratory maxima of a moving average representation of the sampled external respiratory signal; and
    defining the set of respiratory intervals for each respiratory cycle by dividing time between each peak inspiratory maximum into equal-time intervals.

11. The method of claim 1, wherein acquiring the volume data and acquiring the respiratory data are implemented simultaneously.

12. A system for dynamic imaging, the system comprising:
    a respiratory monitor to acquire surrogate respiratory data over a plurality of respiratory cycles;
    a scanner to acquire frame data over the plurality of respiratory cycles, the frame data comprising a plurality of frames; and
    one or more processors in communication with the respiratory monitor and the scanner, the one or more processors being configured to:
        divide each respiratory cycle of the plurality of respiratory cycles into a set of respiratory intervals based on the surrogate respiratory data;
        correlate the frame data produced over the plurality of respiratory cycles with a respective respiratory interval of the set of respiratory intervals;
        determine average frame data per respiratory interval of the set of respiratory intervals based on the frame data from the plurality of respiratory cycles correlated with the respective respiratory interval;

select, for each respiratory interval, a subset of the frame data correlated with the respective respiratory interval, using the average frame data for the respective respiratory interval as a template; and construct a respective composite three-dimensional image for each respiratory interval based on the selected subset of the frame data for each respiratory interval.

13. The system of claim 12, wherein the one or more processors are configured to determine a standard deviation of the frame data for each respiratory interval.

14. The system of claim 13, wherein the one or more processors are configured to normalize the standard deviation based on the average frame data for each respiratory interval.

15. The system of claim 12, wherein the one or more processors are configured to determine a maximum or minimum intensity projection of the frame data for each respiratory interval.

16. The system of claim 12, wherein the one or more processors are configured to:

implement an image registration to compute a similarity metric for the frame data in each respiratory interval from each respiratory cycle of the plurality of respiratory cycles relative to the average frame data for the respiratory interval;

determine, for each respiratory interval, a subset of frames of the frame data that meet a threshold of the similarity metric to select the subset of the frame data for each respiratory interval; and construct a further respective three-dimensional image for each respiratory interval based on an average of the frame data in each subset to construct the respective composite three-dimensional image for each respiratory interval.

17. The system of claim 12, wherein the one or more processors are configured to:

define each respiratory cycle based on peak inspiratory maxima of a moving average representation of the surrogate respiratory data; and defining the set of respiratory intervals for each respiratory cycle by dividing time between each peak inspiratory maximum into equal-time intervals.

18. A magnetic resonance imaging (MRI) apparatus comprising:

an MRI scanner configured to acquire data representing a plurality of two-dimensional slices over a plurality of respiratory cycles; and a control system in communication with the MRI scanner and configured to direct the MRI scanner to implement a series of pulse sequences configured to scan the plurality of two-dimensional image slices over the plurality of respiratory cycles to produce respective scan data representing each two-dimensional image slice, the control system comprising one or more processors configured to:

divide each respiratory cycle of the plurality of respiratory cycles into a set of respiratory intervals;

correlate the scan data produced over the plurality of respiratory cycles with a respective respiratory interval of the set of respiratory intervals;

determine average scan data per respiratory interval of the set of respiratory intervals based on the scan data from the plurality of respiratory cycles correlated with the respective respiratory interval;

select, for each respiratory interval, a subset of the scan data correlated with the respective respiratory interval, using the average frame data for the respective respiratory interval as a template; and construct a respective composite three-dimensional image for each respiratory interval based on the selected subset of the scan data for each respiratory interval.

19. The magnetic resonance imaging (MRI) apparatus of claim 18, wherein the one or more processors are further configured to:

implement an image registration to compute a similarity metric for the data representing the two-dimensional slices in each respiratory interval from each respiratory cycle of the plurality of respiratory cycles relative to the average scan data for the respiratory interval;

determine, for each respiratory interval, a subset of the two-dimensional slices that meet a threshold of the similarity metric to select the subset of the scan data for each respiratory interval; and construct a further respective three-dimensional image for each respiratory interval based on an average of the slices in each subset to construct the respective composite three-dimensional image for each respiratory interval.

* * * * *